US009859584B2

United States Patent
Kabetani et al.

(10) Patent No.: US 9,859,584 B2
(45) Date of Patent: *Jan. 2, 2018

(54) WINDING DEVICE, WINDING METHOD, INSPECTION DEVICE AND STRUCTURE MANUFACTURING METHOD IN WHICH A POSITION OF STUCK TOGETHER FIRST AND SECOND WOUND SHEETS ARE DETECTED VIA INTERFERENCE LIGHT GENERATED USING REFLECTED REFERENCE LIGHT FROM A REFERENCE SURFACE

(71) Applicant: Panasonic Intellectual Property Management Co., Ltd., Osaka (JP)

(72) Inventors: Yasuhiro Kabetani, Hokkaido (JP); Tomotaka Furuta, Osaka (JP); Nobuo Hara, Osaka (JP); Shohei Aoki, Osaka (JP); Seiji Hamano, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/193,568

(22) Filed: Jun. 27, 2016

(65) Prior Publication Data

US 2016/0308240 A1    Oct. 20, 2016

Related U.S. Application Data

(63) Continuation of application No. 14/388,993, filed as application No. PCT/JP2013/000346 on Jan. 24, 2013, now Pat. No. 9,404,733.

(30) Foreign Application Priority Data

May 11, 2012 (JP) ................................ 2012-109780

(51) Int. Cl.
*H01M 10/04* (2006.01)
*G01B 11/14* (2006.01)
(Continued)

(52) U.S. Cl.
CPC ........ *H01M 10/0409* (2013.01); *B65H 81/00* (2013.01); *G01B 9/02004* (2013.01);
(Continued)

(58) Field of Classification Search
CPC ... H01M 10/0409; B65H 39/16; B65H 18/00; B65H 39/14; Y10T 29/4911;
(Continued)

(56) References Cited

U.S. PATENT DOCUMENTS 4,844,312 A    7/1989  Gomi
5,739,904 A *  4/1998  Berger ................ B65H 63/006
                                                     356/238.2
(Continued)

FOREIGN PATENT DOCUMENTS

CN    102192896    9/2011
JP    2-136989     5/1990
(Continued)

OTHER PUBLICATIONS

International Search Report dated Feb. 26, 2013 in International (PCT) Application No. PCT/JP2013/000346.
(Continued)

*Primary Examiner* — Michael P Lapage
(74) *Attorney, Agent, or Firm* — Wenderoth, Lind & Ponack, L.L.P.

(57) ABSTRACT

Provided is a winding apparatus that is provided with a splitter that splits radiant light from a light source unit into measurement light applied to a side face part of a first sheet and a second sheet and reference light applied to a reference surface, an interference detector that detects interference
(Continued)

light formed by interference between the reference light reflected by the reference surface and the measurement light reflected by the side face part, a position detector that detects the position of the first sheet and the position of the second sheet on the basis of the detected interference light, and a decision processor that decides the quality of the wound body on the basis of the detected positions of the first sheet and the second sheet.

25 Claims, 11 Drawing Sheets

(51) Int. Cl.
| | | |
|---|---|---|
| *G01B 11/00* | (2006.01) | |
| *G01B 9/02* | (2006.01) | |
| *G01N 21/47* | (2006.01) | |
| *G01N 21/89* | (2006.01) | |
| *B65H 81/00* | (2006.01) | |
| *H01G 4/005* | (2006.01) | |
| *H01G 4/32* | (2006.01) | |
| *H01G 13/02* | (2006.01) | |
| *B65H 39/16* | (2006.01) | |
| *B65H 18/00* | (2006.01) | |

(52) U.S. Cl.
CPC .......... *G01B 9/02091* (2013.01); *G01B 11/00* (2013.01); *G01B 11/14* (2013.01); *G01N 21/4795* (2013.01); *G01N 21/8901* (2013.01); *H01G 4/005* (2013.01); *H01G 4/32* (2013.01); *H01G 13/02* (2013.01); *B65H 18/00* (2013.01); *B65H 39/16* (2013.01); *B65H 2553/41* (2013.01); *Y10T 29/4911* (2015.01); *Y10T 29/49119* (2015.01)

(58) Field of Classification Search
CPC ......... Y10T 29/49119; Y10T 29/49114; Y10T 29/49112; Y10T 29/49108; G01B 11/14; G01B 11/00; G01B 9/02004; G01B 9/02091; G01N 21/4795; G01N 21/8901
See application file for complete search history.

(56) References Cited

U.S. PATENT DOCUMENTS

| | | |
|---|---|---|
| 6,497,384 B1 | 12/2002 | Fujiwara et al. |
| 8,670,126 B2 | 3/2014 | Kabetani et al. |
| 2003/0029959 A1 | 2/2003 | Fujiwara et al. |
| 2006/0123622 A1 | 6/2006 | Guy |
| 2007/0077045 A1 | 4/2007 | Kato |
| 2010/0066004 A1* | 3/2010 | Shiraishi ................. B65H 7/14 271/3.16 |
| 2010/0281685 A1 | 11/2010 | Hori |

FOREIGN PATENT DOCUMENTS

| | | |
|---|---|---|
| JP | 11-51629 | 2/1999 |
| JP | 11-326183 | 11/1999 |
| JP | 2000-337827 | 12/2000 |
| JP | 2003-139688 | 5/2003 |
| JP | 2006-145298 | 6/2006 |
| JP | 2006-266834 | 10/2006 |
| JP | 2007-101263 | 4/2007 |
| JP | 2007-256177 | 10/2007 |
| JP | 2008-24476 | 2/2008 |
| JP | 2011-158395 | 8/2011 |
| JP | 2011-174920 | 9/2011 |
| JP | 2012-63330 | 3/2012 |

OTHER PUBLICATIONS

International Preliminary Report on Patentability and Written Opinion of the International Searching Authority dated Nov. 20, 2014 in International (PCT) Application No. PCT/JP2013/000346.

Chinese Office Action dated Mar. 30, 2015 in corresponding Chinese Patent Application No. 201380016049.X, with English translation.

* cited by examiner

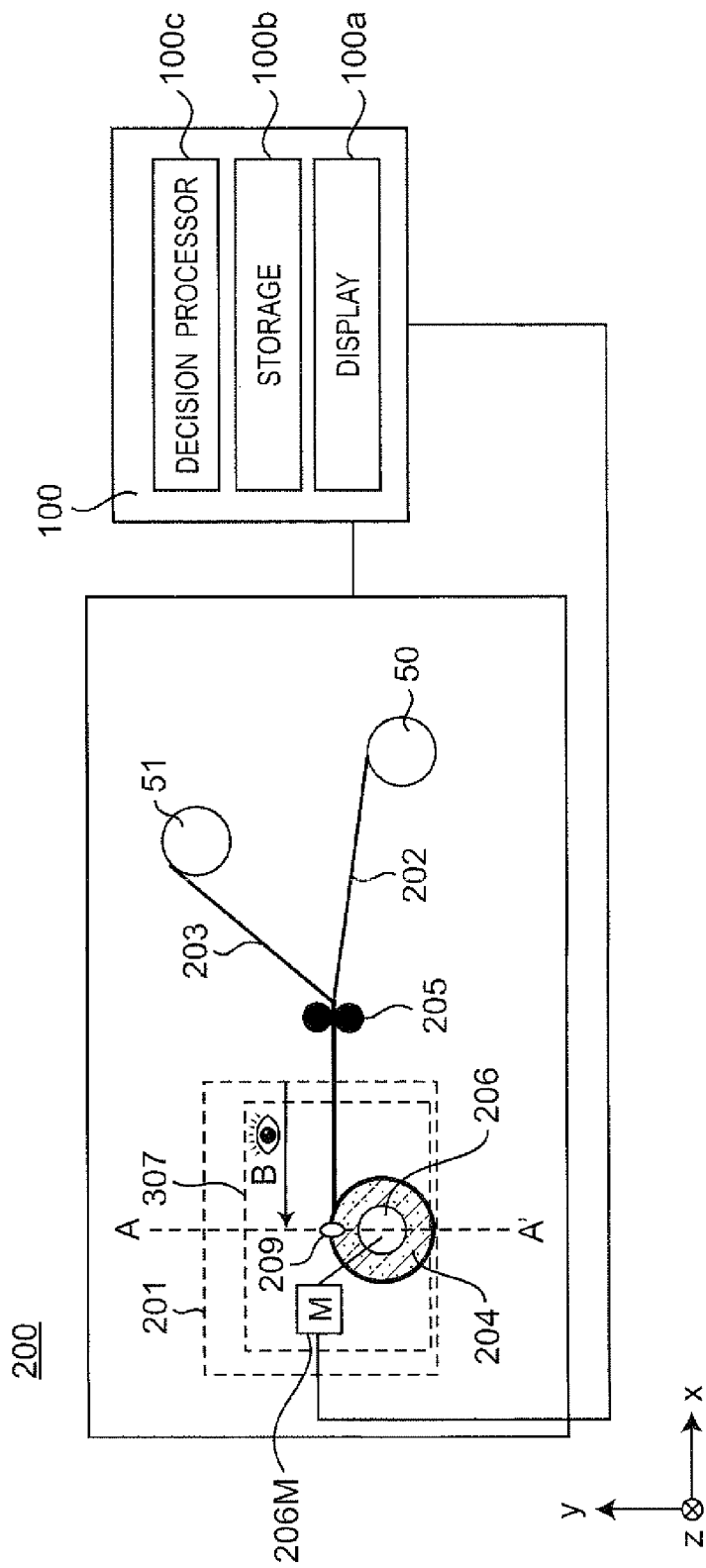

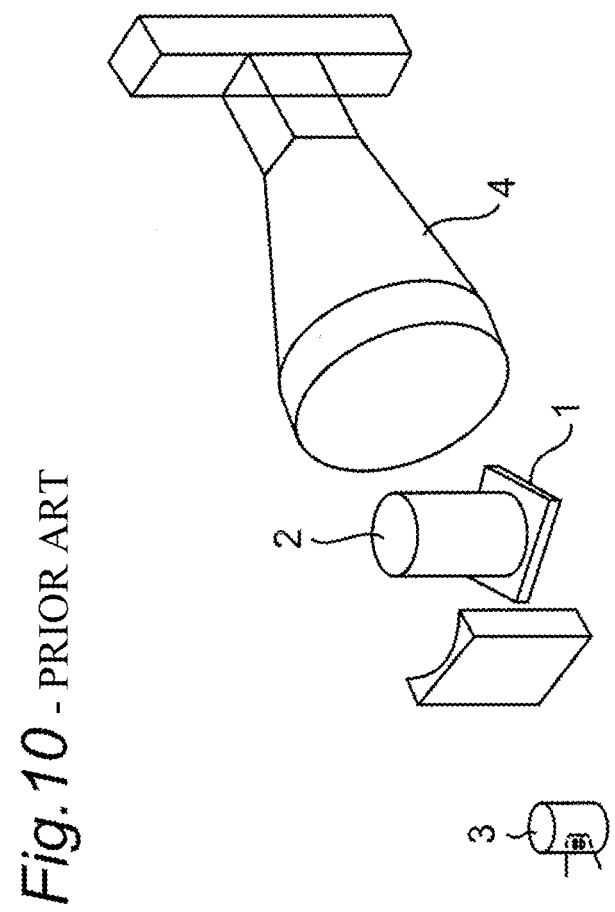
Fig. 10 - PRIOR ART

WINDING DEVICE, WINDING METHOD, INSPECTION DEVICE AND STRUCTURE MANUFACTURING METHOD IN WHICH A POSITION OF STUCK TOGETHER FIRST AND SECOND WOUND SHEETS ARE DETECTED VIA INTERFERENCE LIGHT GENERATED USING REFLECTED REFERENCE LIGHT FROM A REFERENCE SURFACE

TECHNICAL FIELD

The present invention relates to a winding apparatus, a winding method, an inspection device, and a structural object manufacturing method.

BACKGROUND ART

In a wound body formed by winding a band-shaped sheet member such as an electrode of a lithium ion battery and a film capacitor, it is important to inspect winding deviation of the sheet member because of the characteristics thereof. As a device for inspecting winding deviation, a device as illustrated in FIG. 10 is described in Patent Literature 1 as conventional art.

In FIG. 10, an inspection object 2 is placed on a table 1. The inspection object 2 is a wound body in which the winding of a sheet member has been completed. X-rays are applied to one side face of the inspection object 2 placed on the table 1 from an X-ray applicator 3. A TV camera 4 images the other side face of the inspection object 2. An X-ray transmission image of the inspection object 2 is obtained by the imaging using the TV camera 4. The winding deviation of the inspection object 2 is inspected on the basis of the X-ray transmission image in the conventional art.

CITATION LIST

Patent Literature

Patent Literature 1: Japanese Unexamined Patent Publication No. 11-51629

SUMMARY OF INVENTION

Technical Problem

However, the conventional art has a problem of the risk of radiation exposure to operators because of the usage of X-rays.

The present invention solves the above conventional problem and an object of the present invention is to provide a winding apparatus, a winding method, an inspection device, and a structural object manufacturing method, each of which can perform inspection without using X-rays.

Solution to Problem

In accomplishing these and other aspects, according to an aspect of the present invention, there is provided a winding apparatus that winds a first sheet and a second sheet that are stuck together on a winding core to form a wound body, the winding apparatus comprising:

a light source unit that emits radiant light;

a splitter that splits the radiant light into measurement light applied to a side face part of the first sheet and the second sheet stuck together and reference light applied to a reference surface;

an interference detector that detects interference light formed by interference between the reference light reflected by the reference surface and the measurement light reflected by the side face part;

a position detector that detects a position of the first sheet and a position of the second sheet based on the detected interference light; and a decision processor that decides quality of the wound body based on the detected positions of the first sheet and the second sheet.

In accomplishing these and other aspects, according to another aspect of the present invention, there is provided an inspection device that inspects a component having a first sheet and a second sheet that are stuck together, the inspection device comprising:

a light source unit that emits radiant light;

a splitter that splits the radiant light into measurement light applied to a side face part of the first sheet and the second sheet and reference light applied to a reference surface;

an interference detector that detects interference light formed by interference between the reference light reflected by the reference surface and the measurement light reflected by the side face part;

a position detector that detects a position of the first sheet and a position of the second sheet based on the detected interference light; and a decision processor that decides quality of the component based on the detected positions of the first sheet and the second sheet.

In accomplishing these and other aspects, according to another aspect of the present invention, there is provided a winding method that performs an inspection step while winding a first sheet and a second sheet that are stuck together on a winding core to form a wound body, the inspection step comprising:

applying measurement light to a side face part of the first sheet and the second sheet stuck together and applying reference light to a reference surface;

detecting interference light formed by interference between the reference light reflected by the reference surface and the measurement light reflected by the side face part;

detecting a position of the first sheet and a position of the second sheet based on the detected interference light; and deciding quality of the wound body based on the detected positions of the first sheet and the second sheet.

In accomplishing these and other aspects, according to another aspect of the present invention, there is provided a structural object manufacturing method comprising:

preparing the wound body formed by the winding method according to the above aspect; and manufacturing a structural object using the wound body.

In accomplishing these and other aspects, according to another aspect of the present invention, there is provided a structural object manufacturing method comprising:

inspecting the component using the inspection device according to the above aspect; and manufacturing a structural object using the inspected component.

Advantageous Effects of Invention

By the above construction of the aspects of the present invention, the inspection can be performed without using X-rays.

BRIEF DESCRIPTION OF DRAWINGS

These and other aspects and features of the present invention will become clear from the following description taken in conjunction with the preferred embodiments thereof with reference to the accompanying drawings, in which:

FIG. 1A is a schematic view of a winding apparatus in a first embodiment;

FIG. 10 is a schematic configuration view of a conventional winding deviation inspection technique in Patent Literature 1.

DESCRIPTION OF EMBODIMENTS

Figure 1B:
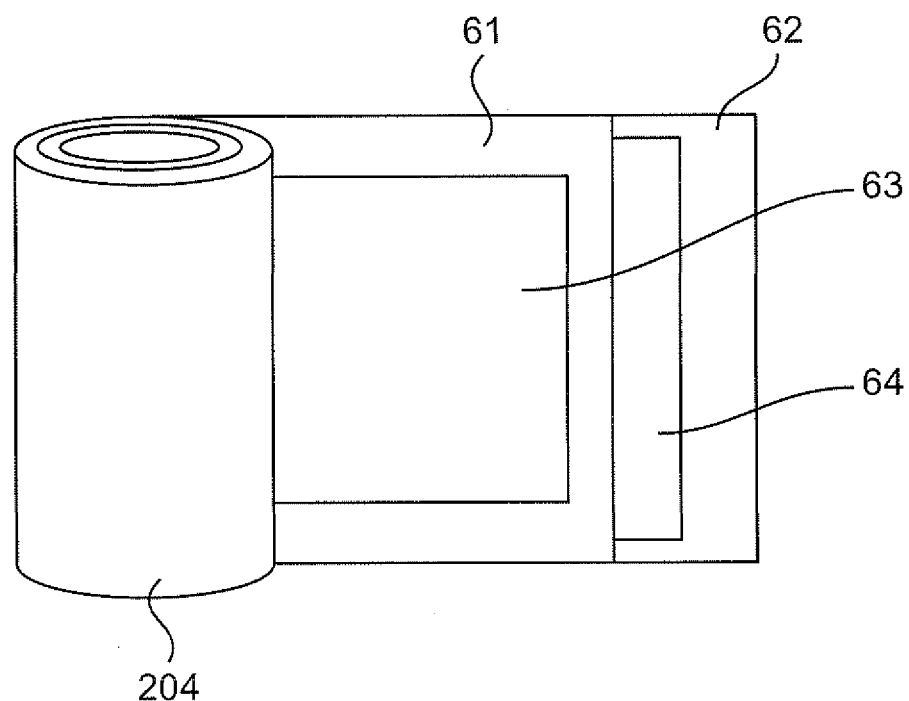
FIG. 1B is a perspective view of a lithium ion battery as an example of an inspection object of the winding apparatus.

Hereinbelow, embodiments of the present invention will be described with reference to the drawings. The same components will be denoted by the same reference numerals throughout the accompanying drawings.

First Embodiment

<Summary of Winding Apparatus 200>

FIG. 1A is a schematic view of a winding apparatus 200 in a first embodiment of the present invention.

In FIG. 1A, the winding apparatus 200 is provided with an SS-OCT device 201. The winding apparatus 200 is a device that sticks a first sheet member 202 and a second sheet member 203 together and that winds the stuck first and second sheet members 202, 203 on a winding core 206 to form a wound body 204. The first sheet member 202 is an example of a first sheet. The second sheet member 203 is an example of a second sheet. In the first embodiment, light is applied to one side of the wound body 204 including the first sheet member 202 and the second sheet member 203 from the SS-OCT device 201 to thereby inspect the winding deviation of the first sheet member 202 or the second sheet member 203 which forms the wound body 204. When winding the first sheet member 202 and second sheet member 203 which are stuck together on the winding core 206 to form the wound body 204, a known temporary fixing member such as a temporary fixing tape may be appropriately used in order to more reliably maintain a wound state of the outermost part of the first sheet member 202 and the second sheet member 203 to prevent rewinding.

The winding apparatus 200 is provided with a first supply reel 50, a second supply reel 51, a sticking roll 205, the winding core 206, a winding core rotation drive unit 206M, and a winding controller 100.

The winding core rotation drive unit 206M includes a motor and the like, and drives the winding core 206 to rotate on the basis of information from the winding controller 100.

The winding controller 100 is provided with a display 100a, a storage 100b, and a decision processor 100c, and controls a winding operation of the winding apparatus 200.

The display 100a displays whether the formed wound body 204 is an OK product or an NG product.

The storage 100b stores therein the fact that the wound body 204 is an NG product associated the serial number assigned to the wound body 204.

The decision processor 100c decides the quality (OK or NG) of the wound body 204 on the basis of a position detected by an OCT processor 314 (described below, see FIG. 2).

The first sheet member 202 and the second sheet member 203 are respectively wound in a roll shape on the first supply reel 50 and the second supply reel 51, and placed inside the winding apparatus 200. The first sheet member 202 is rewound from the first supply reel 50, and supplied to the sticking roll 205. The second sheet member 203 is rewound from the second supply reel 51, and supplied to the sticking roll 205. The first sheet member 202 and the second sheet member 203 are stuck together by the sticking roll 205, and then reach the winding core 206 to form the wound body 204 around the winding core 206.

The wound body 204 is, for example, a member that constitutes a lithium ion battery. As illustrated in FIG. 1B, the wound body 204 constituting a lithium ion battery includes four sheet members in total including a positive electrode 63, a negative electrode 64, and two separators 61, 62 as insulators interposed between the positive electrode 63 and the negative electrode 64. However, for the purpose of easy explanation, in the following description, the number of sheet members included in the wound body 204 is two. Specifically, the first sheet member 202 is defined as the positive electrode 63 as an example of an electrode as a conductor, and the second sheet member 203 is defined as the separator 61 as an insulator.

The sticking roll 205 includes a pair of rolls. The first sheet member 202 and the second sheet member 203 are sandwiched between the rolls to thereby laminate the first sheet member 202 and the second sheet member 203.

The SS-OCT device 201 is a light interference signal measurement device that uses Swept Source Optical Coherence Tomography (SS-OCT). Optical Coherence Tomography (OCT) is a measurement method using a light interference phenomenon. In OCT, radiant light from a light source is split into reference light and measurement light. The reference light is allowed to enter a reference surface, and the measurement light is allowed to enter a measurement object. Then, the reference light reflected by the reference surface and the measurement light reflected by the measurement object are allowed to interfere with each other to thereby detect an interference signal. The position of the measurement object is detected on the basis of the detected interference signal.

The OCT is roughly classified into two types including Time Domain Optical Coherence Tomography (TD-OCT) which requires scanning of a reference surface and Fourier Domain Optical Coherence Tomography (FD-OCT) which does not require scanning of a reference surface. Further, the FD-OCT includes two types including a spectrometer type and a swept source type. In particular, swept source type FD-OCT is called SS-OCT. In the SS-OCT, interference light is detected while temporally changing the frequency of light emitted from a light source.

Figure 2:
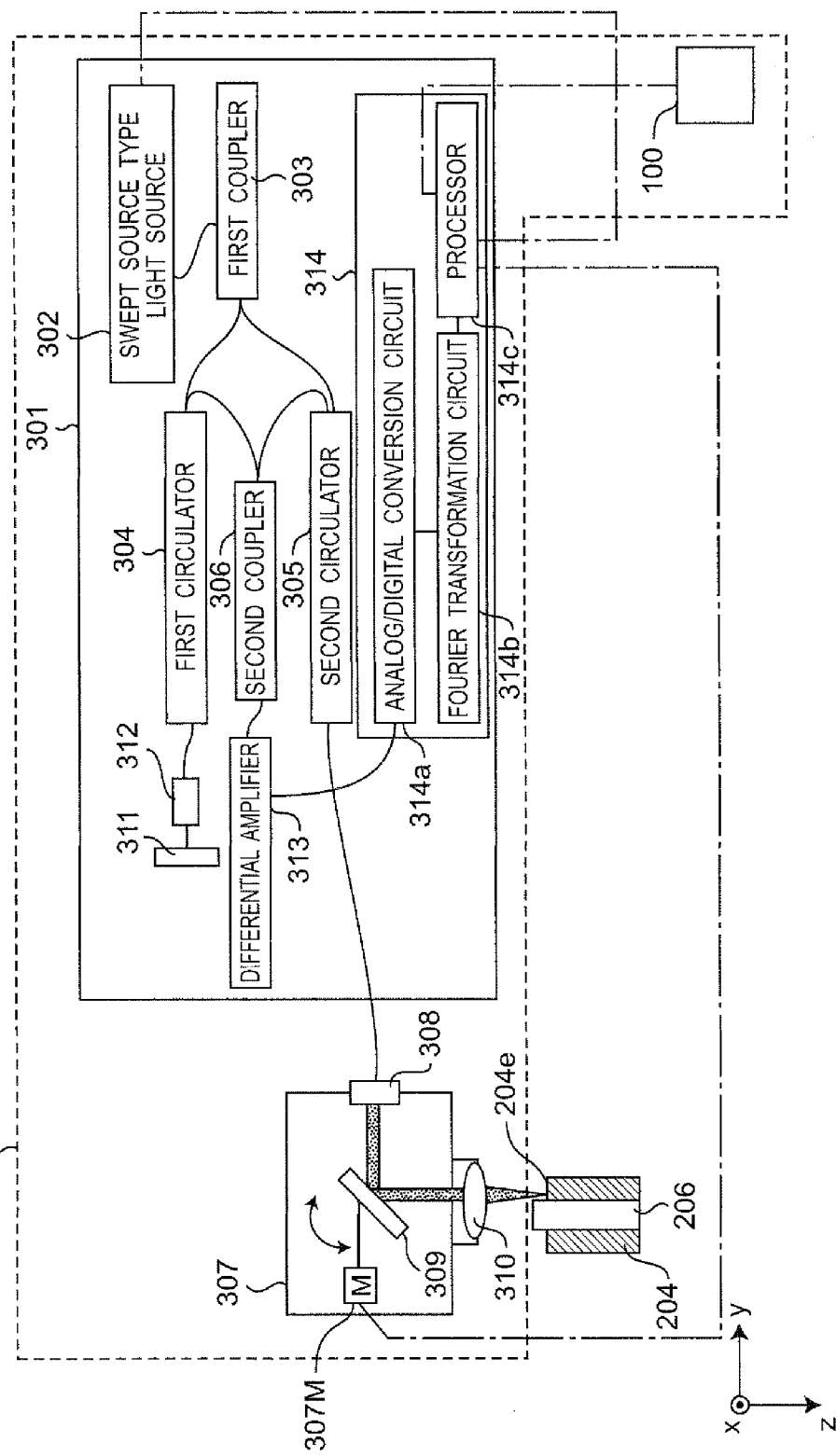
FIG. 2 is a configuration view of an inspection device for inspecting the winding deviation of the winding apparatus, specifically, a cross-sectional view taken along line A-A' of FIG. 1A observed from arrow B.

FIG. 2 illustrates a schematic configuration of the SS-OCT device 201.

The SS-OCT device 201 is provided with an optical fiber interferometer 301 and a measurement head 307. The optical fiber interferometer 301 is provided with a swept source type light source 302 which functions as an example of a light source unit. The measurement head 307 functions as an example of an optical member.

The optical fiber interferometer 301 is provided with the swept source type light source 302 which changes the wavelength of radiant light to be emitted. A light emission port for emitting radiant light from the swept source type light source 302 is connected to a light reception port of a first coupler 303. The first coupler 303 functions as an example of a splitter which splits light into two kinds of light at a fixed ratio. The first coupler 303 includes two light outlet ports, specifically, a first light outlet port and a second light outlet port. The first light outlet port is connected to a first circulator 304. The second light outlet port is connected to a second circulator 305. That is, radiant light from the swept source type light source 302 is split into measurement light and reference light in the first coupler 303. The measurement light enters the second circulator 305. The reference light enters the first circulator 304.

The second circulator 305 is connected to a light reception port of a second coupler 306, and also connected to the measurement head 307 located outside the optical fiber interferometer 301. Therefore, the measurement light from the first coupler 303 enters the measurement head 307. On the other hand, the measurement light from the measurement head 307 enters the second coupler 306.

The measurement head 307 is provided with an irradiation collimator lens 308, a galvano mirror 309, and a beam diameter forming mechanism 310.

The irradiation collimator lens 308 is connected to the second circulator 305.

The galvano mirror 309 is disposed inside the measurement head 307.

The beam diameter forming mechanism 310 is arranged between the galvano mirror 309 and the wound body 204, and forms a spot diameter of the measurement light. The wound body 204 is an example of a measurement object.

The measurement light that has entered the irradiation collimator lens 308 from the second circulator 305 is formed into parallel light by the irradiation collimator lens 308. Then, the measurement light formed into parallel light passes through the galvano mirror 309, and is collected by the beam diameter forming mechanism 310. Then, the measurement light emitted from the beam diameter forming mechanism 310 is applied to an end face (side face part 204e) of the wound body 204. The measurement light reflected (or back-scattered) by the side face part 204e passes through the beam diameter forming mechanism 310, and then enters the second circulator 305. Further, the measurement light that has entered the second circulator 305 enters the second coupler 306.

On the other hand, the reference light emitted from the first circulator 304 enters a reference collimator lens 312. The reference collimator lens 312 allows the reference light to enter a reference surface 311, and allows the reference light reflected by the reference surface 311 to enter the first circulator 304. The first circulator 304 is connected to a light reception port of the second coupler 306.

In the second coupler 306, interference light is formed from the measurement light from the second circulator 305 and the reference light from the first circulator 304. Therefore, the second coupler 306 functions as an example of a multiplexing unit.

A differential amplifier 313 differential-transmits an optical beat signal of the interference light formed in the second coupler 306 to the OCT processor 314. The frequency of radiant light emitted from the swept source type light source 302 varies with the lapse of time. Therefore, there arises a difference in the frequency depending on the amount of time delay between the reference light and the measurement light which interfere with each other in the second coupler 306. The frequency difference constitutes the optical beat signal of interference light.

The OCT processor 314 is provided with an analog/digital conversion circuit (analog/digital conversion unit) 314a, a Fourier transformation circuit (Fourier transformation unit) 314b, and a processor 314c. The Fourier transformation circuit 314b functions as an interference light detector (interference detector). The processor 314c functions as an image acquisition unit and a position detector.

The processor 314c may be configured so as to serve as both the interference detector and the position detector.

The analog/digital conversion circuit 314a performs analog/digital conversion of a time waveform of the optical beat signal of the interference light formed in the second coupler 306.

The Fourier transformation circuit 314b is connected to the analog/digital conversion circuit 314a, and detects the optical beat signal which is a signal based on the interference light from the analog/digital conversion circuit 314a. The Fourier transformation circuit 314b Fourier-transforms the detected signal to perform frequency analysis. An SS-OCT signal which indicates the intensity distribution of the interference light is obtained from a result of the frequency analysis.

The Fourier-transformed information is input to the processor 314c from the Fourier transformation circuit 314b. The processor 314c calculates a position z1 and a position z2 of reflection surfaces of the first sheet member 202 and the second sheet member 203 in the wound body 204 at a position to which the measurement light is applied on the basis of the information (SS-OCT signal) input from the Fourier transformation circuit 314b (see FIG. 4A). The frequency analysis may also be performed in the processor 314c.

An output unit of the processor 314c is electrically connected to the swept source type light source 302 and a drive unit 307M for driving the galvano mirror 309 and the like of the measurement head 307, and controls operations of the swept source type light source 302 and the galvano mirror 309. The output unit of the processor 314c is also connected to the winding controller 100. The winding controller 100 performs a predetermined operation such as inspection of winding deviation on the basis of information from the processor 314c.

In the first embodiment, the TD-OCT may be employed. However, in order to increase the speed of the measurement, for example, SS-OCT or FD-OCT which can perform one-dimensional scanning called A-scan at 10 kHz or more is preferably used.

<Placement Position of Measurement Head>

FIG. 2 illustrates the wound body 204 and the winding core 206 in a cross-sectional view taken along line A-A' of FIG. 1A viewed from arrow B. As illustrated in FIG. 2, the measurement head 307 is placed on a rotation axis of the winding core 206. Such placement makes it possible to apply the measurement light to the wound body 204 along the z-axis direction which is parallel to the rotation axis of the wound body 204 from the measurement head 307.

Further, a rotation axis of the galvano mirror 309 in the measurement head 307 is arranged in parallel to the x-axis. Such a configuration makes it possible to move an irradiation position of the measurement light toward the y-axis direction.

<Winding Method in First Embodiment>

Figure 3:
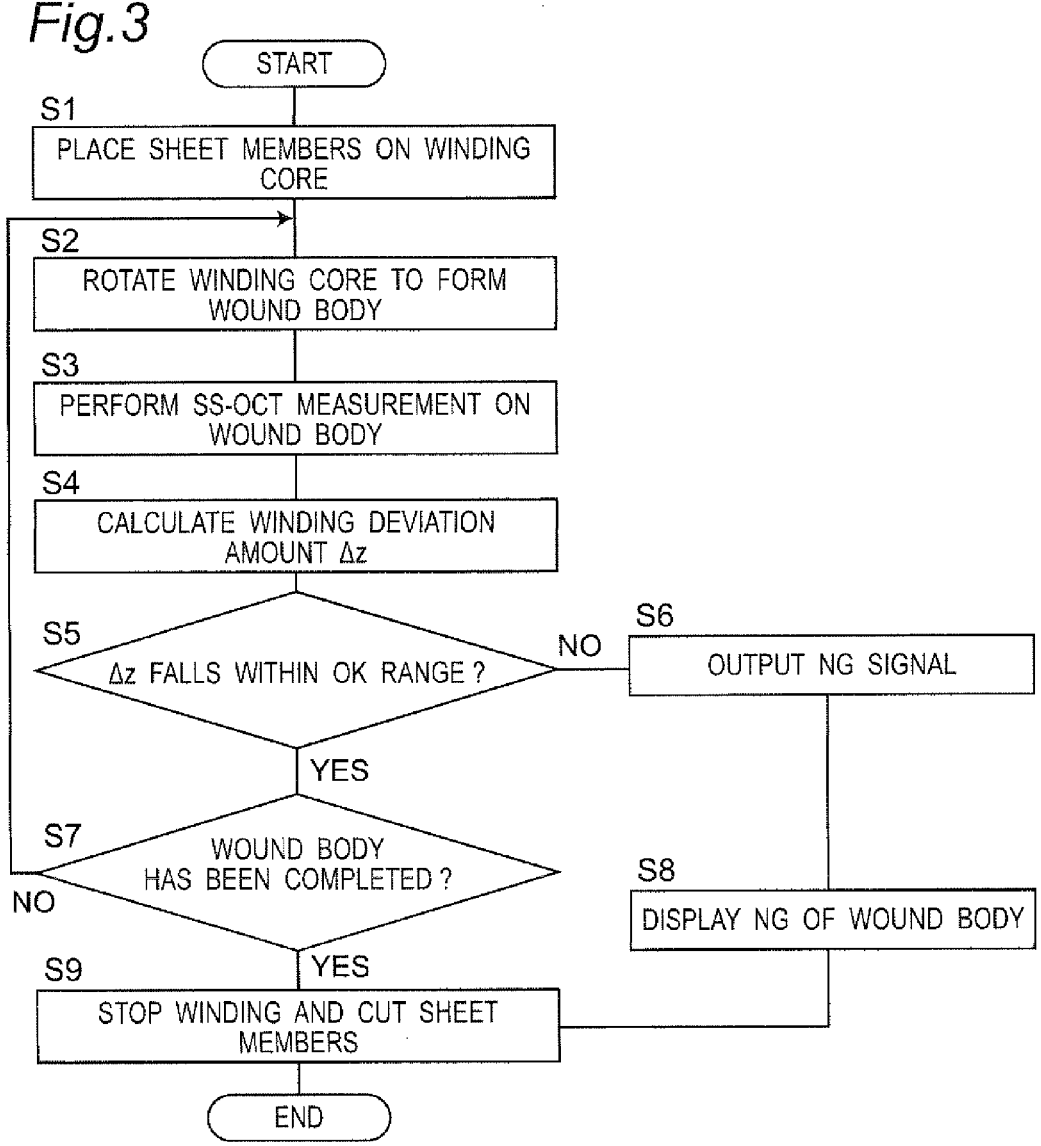
FIG. 3 is a flow chart illustrating a winding method performed by the winding apparatus according to the first embodiment.

FIG. 3 is a flow chart illustrating a winding method performed by the winding apparatus 200 of FIG. 1A. Here, description will be made with reference to FIGS. 1A, 2, and 3.

In step S1, the first sheet member 202 and the second sheet member 203 of FIG. 1A are placed so that the first sheet member 202 and the second sheet member 203 can be wound on the winding core 206. Step S1 may be performed by an operator, or may also be automatically performed by a grasping unit which grasps the first sheet member 202 and the second sheet member 203. As a method for placing the first sheet member 202 and the second sheet member 203 on the winding core 206, for example, the first sheet member 202 and the second sheet member 203 are held on an open/close type slit provided in the winding core 206.

Then, in step S2, the winding controller 100 controls the winding core rotation drive unit 206M to rotate the winding core 206 in the counterclockwise direction. As a result, the first sheet member 202 and the second sheet member 203 are wound on the winding core 206, and the wound body 204 is thereby formed around the winding core 206.

Then, in step S3, SS-OCT measurement using the SS-OCT device 201 is performed on the wound body 204.

The SS-OCT measurement will be specifically described below.

The SS-OCT device 201 of FIG. 2 performs the measurement while changing the wavelength of radiant light emitted from the swept source type light source 302. The range of changing the wavelength is, for example, 1300 nm±50 nm. The operation of the swept source type light source 302 is controlled by the processor 314c.

Radiant light from the swept source type light source 302 is applied to the wound body 204 from the direction of the rotation axis of the wound body 204, or the z-axis direction. The measurement light applied to the wound body 204 is reflected by the end face (side face part 204e) of the wound body 204. The reflected measurement light includes light reflected by the first sheet member 202 and light reflected by the second sheet member 203. The measurement light reflected by the wound body 204 travels to the second coupler 306. In the second coupler 306, the measurement light reflected by the wound body 204 and the reference light reflected by the reference surface 311 interfere with each other to form interference light. An optical beat signal of the interference light passes through the differential amplifier 313, and is detected in the OCT processor 314. The OCT processor 314 performs frequency analysis on the detected optical beat signal to thereby obtain an SS-OCT signal. Then, the OCT processor 314 calculates the position z1 of the reflection surface of the first sheet member 202 of FIG. 1A and the position z2 of the reflection surface of the second sheet member 203 of FIG. 1A on the basis of the SS-OCT signal. The position z1 indicates the position of the end face of a long side (side face part) of the first sheet member 202 in the z-axis direction. The position z2 indicates the position of the end face of a long side (side face part) of the second sheet member 203 in the z-axis direction. The long side of the first sheet member 202 indicates a side in the first sheet member 202, the side being parallel to the movement direction of the first sheet member 202. The long side of the second sheet member 203 indicates a side in the second sheet member 203, the side being parallel to the movement direction of the second sheet member 203. Information about the position z1 and the position z2 calculated in the OCT processor 314 is output to the winding controller 100.

Then, in step S4, a winding deviation amount Δz between the first sheet member 202 and the second sheet member 203 is calculated on the basis of the calculated positions z1 and z2. The winding deviation amount Δz will be specifically described below. The winding deviation amount Δz is calculated in the decision processor 100c of the winding controller 100.

Then, in step S5, the decision processor 100c decides whether the winding deviation amount Δz calculated in step S3 falls within an OK range. The OK range indicates a range of the winding deviation amount Δz within which a product can be regarded as anon-defective product. Specifically, the OK range indicates a range of the winding deviation amount Δz that does not cause a problem on the quality of a product. The OK range is previously stored in the storage 100b. The OK range to be previously stored will be described in detail below. When the winding deviation amount Δz does not fall within the OK range (No in step S5), the process proceeds to step S6. On the other hand, when the winding deviation amount Δz falls within the OK range (Yes in step S5), the process proceeds to step S7.

In step S6, an NG signal from the decision processor 100c is transmitted to the display 100a and the winding core rotation drive unit 206M.

Then, in step S8, the fact that the formed wound body 204 is an NG product is displayed on the display 100a. Further, the storage 100b of the winding controller 100 stores therein the fact of NG associated with the serial number or the like assigned to the wound body 204. Such a configuration makes it possible to discard the NG product in the subsequent step by checking information stored in the storage 100b against the serial number or the like of the wound body 204.

On the other hand, in step S7, the decision processor 100c decides whether the wound body 204 has been completed. When the decision processor 100c decides that the wound body 204 has been completed (Yes in step S7), the process proceeds to step S9. Whether the wound body 204 has been completed is decided by the winding controller 100 on the basis of information from an encoder or the like connected to the winding core rotation drive unit 206M. For example, the number of rotations of the winding core 206 is obtained from the information from the encoder, and the decision processor 100c decides whether the obtained number of rotations has reached the number of rotations that is previously stored in the storage 100b. The number of rotations to be previously stored is, for example, 10. When the decision processor 100c decides that the winding of the wound body 204 has not been completed (No in step S7), the process returns to step S2 without stopping the winding, and the SS-OCT measurement is again performed.

When the decision processor 100c decides that the winding of the wound body 204 has been completed, or when an NG signal is output from the decision processor 100c, the winding core rotation drive unit 206M stops the rotation of the winding core 206 in step S9. Then, the first sheet member 202 and the second sheet member 203 are cut by an electrode cutting unit (not illustrated) between the sticking roll 205 and the winding core 206, and the operation is finished.

When performing step S8, step S9 may be performed at the same time.

Steps S3 to S5 are an example of an inspection step. In the present embodiment, performing the inspection step at the same time of forming the wound body 204 makes it possible to shorten the time required from the start of the formation of the wound body 204 until the finish of the inspection.

Further, by performing a step of preparing the wound body 204 formed by the winding method in the first embodiment and a step of manufacturing a structural object using the prepared wound body 204, an example of a structural object manufacturing method can be achieved. Further, another example of the structural object manufacturing method can also include a step of inspecting the wound body 204 as an example of a component using the SS-OCT device 201 as an example of an inspection device and a step of manufacturing a structural object using the inspected wound body 204. As another example of the component, a laminated body formed by laminating the first sheet member 202 and the second sheet member 203 can also be employed.

Examples of the structural object can include a laminated battery and a laminated capacitor which can be both manufactured using the laminated body as another example of the component in addition to a wound battery and a wound capacitor which can be both manufactured using the wound body 204 as an example of the component. In a method for manufacturing a battery (an example of the structural object) as a specific example of the structural object manufacturing method, the wound body 204 is housed inside a case, and a negative electrode and a positive electrode are formed in the case to manufacture the battery. As a more specific structural object manufacturing method, there is a method in which the wound body 204 is put into a nickel-plated iron can (an example of the case), a negative electrode is welded to the bottom of the can, an electrolytic solution is injected, a positive electrode is welded to a lid, and an opening is sealed by a press machine.

<Winding Deviation Amount Δz>

Figure 4A:
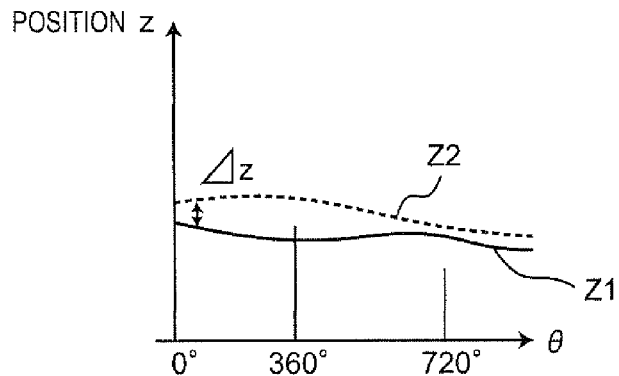
FIG. 4A is a view for explaining a winding deviation amount $\Delta z$, specifically, a view illustrating the relationship between a rotation angle $\theta$ of a winding core and positions Z1, Z2 of the end faces of a wound body.

FIG. 4A is a view illustrating the relationship between the rotation angle θ of the winding core 206 and the position z1 in the z-axis direction in the first sheet member 202 and the position z2 in the z-axis direction in the second sheet member 203 of FIG. 1A. The horizontal axis of FIG. 4A represents the rotation angle θ which indicates the rotation angle of the winding core 206. When θ=0°, the winding core 206 is located at a winding start position. At the winding start position, the first sheet member 202 and the second sheet member 203 are merely placed, and the winding core 206 is in an unrotated state. For example, when θ=360°, the winding core 206 makes one rotation in the counterclockwise direction, and the first sheet member 202 and the second sheet member 203 are each wound by a length corresponding to the single circumference of the winding core 206.

The vertical axis of FIG. 4A represents the position z. On the vertical axis, when a value of the position z becomes larger (located on the upper part of the graph), the position z is located at the front side in the drawing sheet of FIG. 1A. On the other hand, when a value of the position z becomes smaller (located on the lower part of the graph), the position z is located on the deep side in the drawing sheet of FIG. 1A. That is, the graph of FIG. 4A indicates that the position z1 is located on the deep side in the sheet of FIG. 1A with respect to the position z2.

In the first embodiment, the winding deviation amount Δz is the difference between the position z1 and the position z2 at some rotation angle θ, and represented by Δz=z1−z2.

Figure 4B:
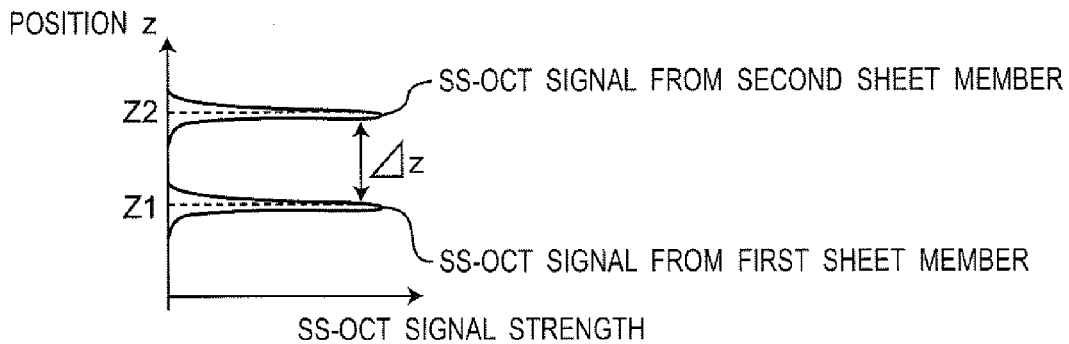
FIG. 4B is a view for explaining the winding deviation amount $\Delta z$, specifically, a view illustrating the relationship between an SS-OCT signal and a position z obtained when $\theta=360°$.
Figure 4C:
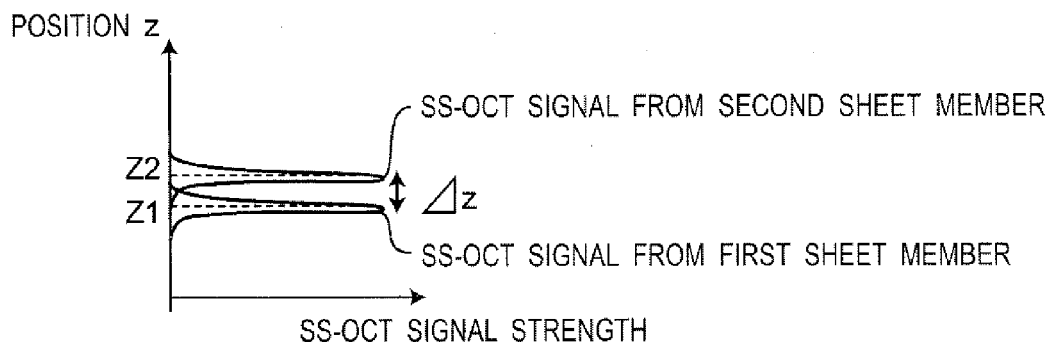
FIG. 4C is a view for explaining the winding deviation amount $\Delta z$, specifically, a view illustrating the relationship between an SS-OCT signal and a position z obtained when $\theta=720°$.

FIG. 4B is a view illustrating the relationship between an SS-OCT signal strength and the position z obtained when θ=360° in FIG. 4A. FIG. 4C is a view illustrating the relationship between the SS-OCT signal strength and the position z obtained when θ=720° in FIG. 4A.

The processor 314c of the SS-OCT device 201 measures two peak positions of the obtained SS-OCT signal as the position z1 of the first sheet member 202 and the position z2 of the second sheet member 203. However, for example, another signal processing method such as edge detection with respect to the SS-OCT signal may be used instead of the detection of the peak positions.

In the present embodiment, it is sufficient to measure the winding deviation amount $\Delta z$. Therefore, when two peaks are obtained in the SS-OCT signal, it is not necessary to distinguish from which sheet member each of the two peaks comes. However, the two peaks (two SS-OCT signals) may be distinguished using a difference in the reflectance with respect to the measurement light between the first sheet member 202 and the second sheet member 203. Specifically, the fact that metal has higher reflectance to the measurement light than a resin is used. Alternatively, the SS-OCT signals may be distinguished using a difference in a peak shape of the SS-OCT signal because the peak shape of the SS-OCT signal of a resin differs from that of metal. Specifically, the peak shape of the SS-OCT signal of metal is sharper than the peak shape of the SS-OCT signal of a resin. In other words, a half-value width of the peak shape of the SS-OCT signal of metal is narrower than a half-value width of the peak shape of the SS-OCT signal of a resin. By using the difference, the position detector (the processor 314c as an example) detects the position of the metal (first sheet) and the position of the separator (second sheet) made of a resin on the basis of the peak shapes included in the SS-OCT signals (the intensity distribution of the interference light) obtained as a result of the frequency analysis.

The winding controller 100 in FIG. 1A performs the measurement continuously while changing a value of $\theta$ by rotating the winding core 206 by driving the winding core rotation drive unit 206M to rotate. In this manner, the winding deviation amount $\Delta z$ is measured at all rotation angles $\theta$ until the winding is finished.

<OK Range>

When forming a lithium ion battery as the wound body 204, it is necessary to arrange a separator so as to prevent a short circuit between a positive electrode and a negative electrode. In this case, when the winding deviation amount $\Delta z$ is less than a certain value, a short circuit may occur between the positive electrode and the negative electrode. Therefore, a first threshold is used as the threshold of the certain value in the present embodiment. Specifically, the first threshold and the winding deviation amount $\Delta z$ are compared with each other in the decision processor 100c to decide the quality. For example, the first threshold is 50 μm.

On the other hand, also when a value of the winding deviation amount $\Delta z$ is too large, a short circuit may occur. That is, the winding deviation amount is required to be a certain value or less. A second threshold is used as the threshold of the certain value. For example, the second threshold is 1950 μm.

Therefore, a range between the first threshold and the second threshold (inclusive) is previously stored as the OK range in the storage 100b. The decision processor 100c performs the quality decision on the basis of the OK range.

As a criterion of the quality decision, the upper limit threshold and the lower limit threshold may be provided with respect to each of the position z1 and the position z2. However, the position z1 and the position z2 obtained by the SS-OCT measurement are each obtained as a difference between two optical paths, specifically, between a path length "H1" of the reference light from when the reference light is emitted from the first coupler 303 until when the reference light is reflected by the reference surface 311 and enters the second coupler 306 and a path length "H2" of the measurement light from when the measurement light is emitted from the first coupler 303 until when the measurement light is reflected by the wound body 204 and enters the second coupler 306 in the optical fiber interferometer 301 of FIG. 2. For example, when the reference light path length "H1" and the measurement light path length "H2" change in response to variations in the environmental temperature, values of the position z1 and the position z2 also change. Therefore, the accuracy of the decision may be reduced. On the other hand, even when the reference light path length "H1" and the measurement light path length "H2" change, the winding deviation amount $\Delta z$ does not change. Therefore, it is preferred to use the winding deviation amount $\Delta z$ in the decision in terms of the accuracy.

<Size of Irradiation Spot 209>

A preferred spot shape of the measurement light when performing the SS-OCT measurement will be described.

The irradiation spot of the measurement light is formed into an elongated elliptical shape by the beam diameter forming mechanism 310 of the SS-OCT device 201 in FIG. 2. Accordingly, the long axis of the elliptical spot shape is made equal to the total thickness of one set of the sheet members (the first sheet member 202 and the second sheet member 203). Further, the movement direction of the first sheet member 202 and the second sheet member 203 which are stuck together by the sticking roll 205 of FIG. 1A and the long axis of the elliptical spot shape are made perpendicular to each other.

Specifically, when the length of the long axis (the axis parallel to the y-axis of FIG. 1A) of the irradiation spot 209 of the measurement light illustrated in FIG. 1A is denoted by "a", the thickness of the first sheet member 202 is denoted by "T1", and the thickness of the second sheet member 203 is denoted by "T2", the following Equation (1) holds.

$$a = T1 + T2 \qquad \text{Equation (1)}$$

For example, when the total thicknesses of the first sheet member 202 and the second sheet member 203 are 100 μm, a=200 μm.

The reason for making the length "a" of the long axis of the irradiation spot 209 equal to the total thickness of one set of the sheet members (the first sheet member 202 and the second sheet member 203) will be described with reference to FIGS. 5A to 7C.

Figure 5A:
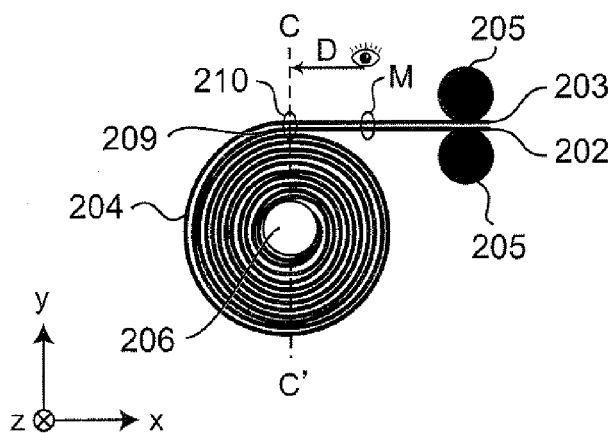
FIG. 5A is a view for explaining an irradiation spot, specifically, a view illustrating the position of the spot in a contact point of the wound body when the length of a long axis of the irradiation spot is 300 μm.

FIG. 5A is a view illustrating a state in which the length "a" of the long axis of the irradiation spot 209 of the measurement light is made sufficiently larger than the total thickness of the set of the sheet members, for example, 300 μm. In this embodiment, the irradiation spot 209 is arranged on a contact point 210.

The contact point 210 indicates a position at which, in a side view illustrating a state in which the sheet members (the first sheet member 202 and the second sheet member 203) are wound on the wound body 204 viewed from the side face (z-axis direction), a part of the sheet members that should be wound first makes contact with the wound body 204 formed by an already wound part of the sheet members. In other words, the contact point 210 indicates a point at which, in a side view of the wound body 204, a tangent line extending from the outer peripheral face of the wound body 204 toward the center between the pair of sticking rolls 205 makes contact with the peripheral face of the wound body 204. The tangent line coincides with the first sheet member 202 and the second sheet member 203 which are stuck together by the sticking roll 205 in a side view viewed from the z-axis direction.

Figure 5B:
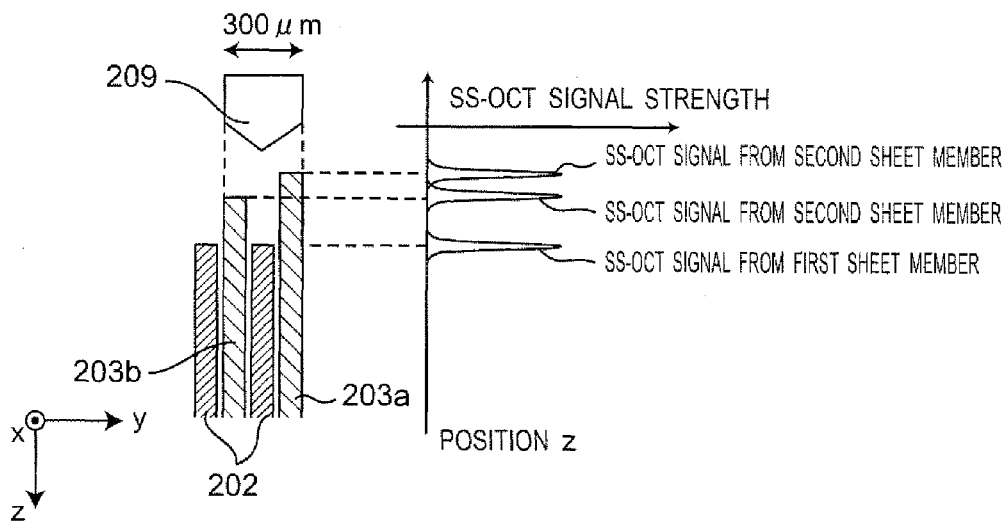
FIG. 5B is a view for explaining the irradiation spot, specifically, a view illustrating the correspondence relationship between a cross-sectional view taken along line C-C' of FIG. 5A observed from arrow D and a view illustrating the relationship between the SS-OCT signal and the position z.
Figure 5C:
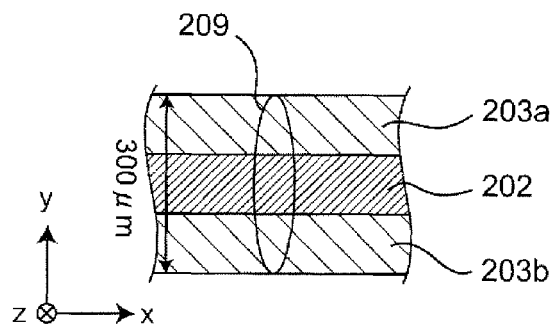
FIG. 5C is a view for explaining the irradiation spot, specifically, an enlarged view of the irradiation spot and the vicinity thereof in FIG. 5A.

FIG. 5B is an explanatory view illustrating the correspondence relationship between a cross-sectional view taken along line C-C' of FIG. 5A observed from arrow D and a view illustrating the relationship between the SS-OCT signal strength and the position z. FIG. 5C is an enlarged view of the irradiation spot 209 and the vicinity thereof in FIG. 5A.

When the length "a" is sufficiently larger than the total thickness of the first sheet member 202 and the second sheet member 203 as illustrated in FIGS. 5A to 5C, there may be disadvantageously obtained, in addition to information about the position of an outermost second sheet member 203a and information about the position of the first sheet member 202 located under the outermost second sheet member 203a, information about the position of a second sheet member 203b that is located on the inner side with respect to the second sheet member 203a by one round. This is because of that the measurement light reflected by the second sheet member 203b is detected. In this case, signals of both the second sheet member 203a and the second sheet member 203b exist in a mixed state in the obtained SS-OCT signal. When the signals are mixed, it is not possible to distinguish the sources of the respective signals, and therefore not possible to accurately measure the winding deviation amount Δz. Therefore, it is necessary to limit the length "a" of the irradiation spot 209 to a certain length or less depending on the total thickness of the first sheet member 202 and the second sheet member 203.

Figure 6A:
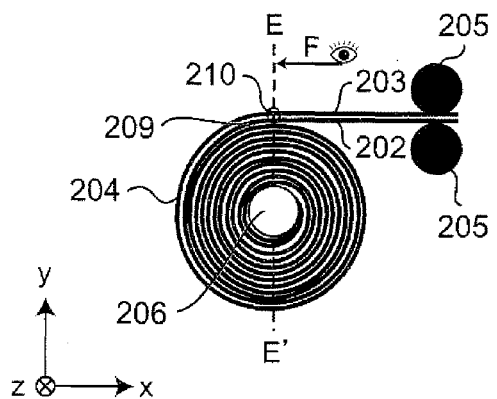
FIG. 6A is a view for explaining an irradiation spot, specifically, a view illustrating the position of the spot in a contact point of the wound body when the length of a long axis of the irradiation spot is 100 μm.
Figure 6B:
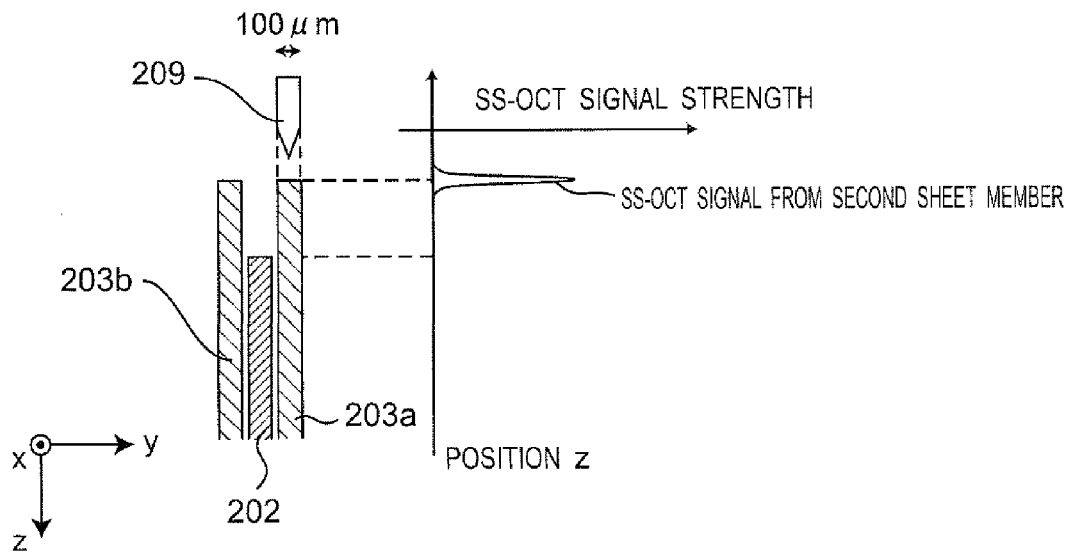
FIG. 6B is a view for explaining the irradiation spot, specifically, a view illustrating the correspondence relationship between a cross-sectional view taken along line E-E' of FIG. 6A observed from arrow F and a view illustrating the relationship between the SS-OCT signal and the position z.
Figure 6C:
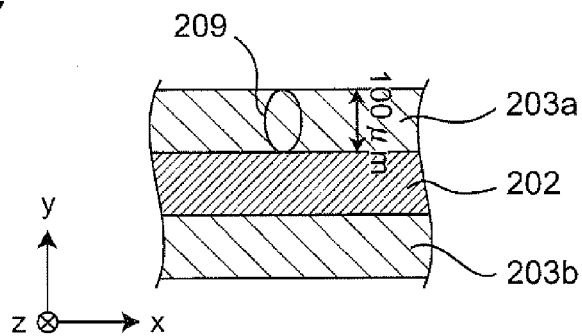
FIG. 6C is a view for explaining the irradiation spot, specifically, an enlarged view of the irradiation spot and the vicinity thereof in FIG. 6A.

On the other hand, FIG. 6A is a view illustrating a case in which the length "a" of the long axis of the irradiation spot 209 is made sufficiently smaller than the total thickness of the first sheet member 202 and the second sheet member 203, for example, 100 μm. FIG. 6B is an explanatory view illustrating the correspondence relationship between a cross-sectional view taken along line E-E' of FIG. 6A observed from arrow F and a view illustrating the relationship between the SS-OCT signal strength and the position z. FIG. 6C is an enlarged view of the irradiation spot 209 and the vicinity thereof in FIG. 6A.

In this case, as illustrated in FIG. 6B, only information about the first sheet member 202 can be obtained. Therefore, in order to obtain the above winding deviation amount Δz=z1−z2, it is necessary to perform the SS-OCT measurement a plurality of times, or prepare a plurality of SS-OCT measurement devices. Thus, it is necessary to set the length "a" of the irradiation spot 209 to a certain length or more depending on the total thickness of the first sheet member 202 and the second sheet member 203.

Figure 7A:
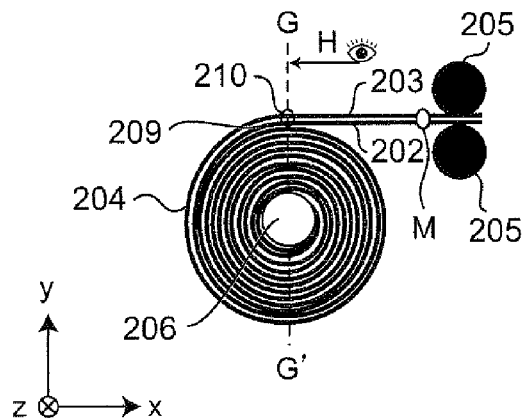
FIG. 7A is a view for explaining an irradiation spot, specifically, a view illustrating the position of the spot in a contact point of the wound body when the length of a long axis of the irradiation spot is 200 μm.
Figure 7B:
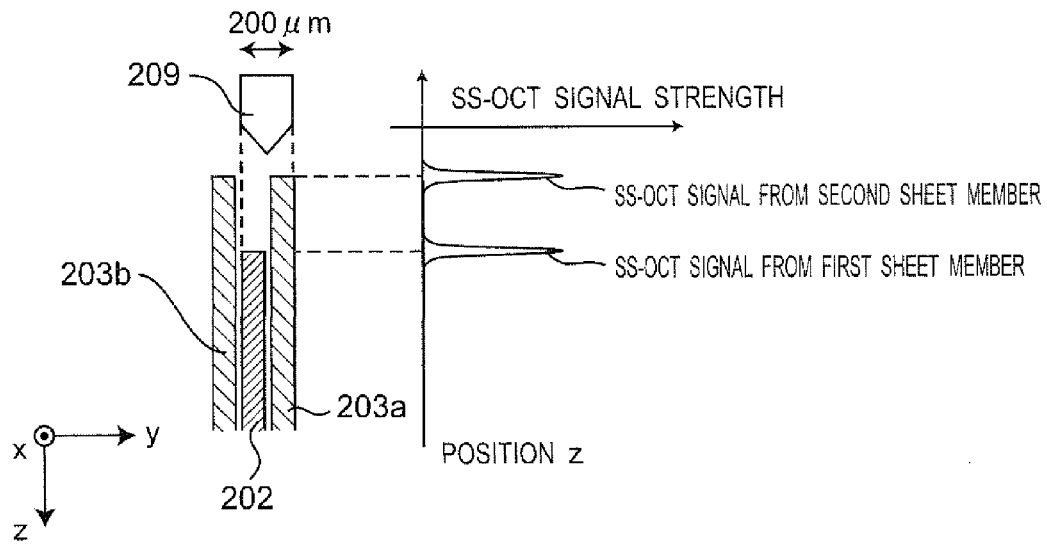
FIG. 7B is a view for explaining the irradiation spot, specifically, a view illustrating the correspondence relationship between a cross-sectional view taken along line G-G' of FIG. 7A observed from arrow H and a view illustrating the relationship between the SS-OCT signal and the position z.
Figure 7C:
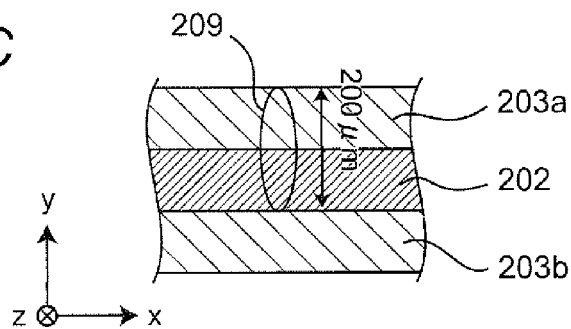
FIG. 7C is a view for explaining the irradiation spot, specifically, an enlarged view of the irradiation spot and the vicinity thereof in FIG. 7A.

Therefore, preferably, the length "a" of the long axis of the irradiation spot 209 is set as illustrated in FIG. 7A. FIG. 7A is a view illustrating a case in which the long axis "a" of the irradiation spot 209 is made equal to the total thickness of the first sheet member 202 and the second sheet member 203, for example, 200 μm. FIG. 7B is an explanatory view illustrating the correspondence relationship between a cross-sectional view taken along line G-G' of FIG. 7A observed from arrow H and a view illustrating the relationship between the SS-OCT signal strength and the position z. FIG. 7C is an enlarged view of the irradiation spot 209 and the vicinity thereof.

In this manner, the length "a" of the long axis of the irradiation spot 209 is set to be made equal to the total thickness of the first sheet member 202 and the second sheet member 203. As a result, only information about the positions of the first sheet member 202 and the second sheet member 203a as one set of sheet members can be obtained, and unnecessary information about the position of the second sheet member 203b is not measured. Therefore, such a length is most desirable.

A specific range of the length "a" of the long axis is desirably 90% or more and 110% or less of the total thickness of the first sheet member 202 and the second sheet member 203 which are stuck together. This range makes it possible to simultaneously measure information about the position of the first sheet member 202 and information about the position of the second sheet member 203a while eliminating the influence of the second sheet member 203b which is unnecessary for the measurement. In the present embodiment, the length "a" of the long axis of the irradiation spot 209 is set, for example, to 200 μm±20 μm.

The reason of ±20 μm (90% or more and 110% or less of the total thickness) will be further described.

Setting the length "a" of the long axis to 200 μm or more and 220 μm (110% of the total thickness) or less leads to the following state. The irradiation spot 209 slightly overlaps the second sheet member 203b in addition to the second sheet member 203a, and an SS-OCT signal from the second sheet member 203b is also disadvantageously detected. However, in this case, the area of the second sheet member 203b occupying the irradiation spot 209 is sufficiently small. Therefore, the SS-OCT signal from the second sheet member 203b is hardly detected. However, the inventors of the present application have found out that, when the length "a" of the long axis is made larger than 220 μm (110% of the total thickness), the influence of the SS-OCT signal from the second sheet member 203b becomes large and it is therefore not possible to accurately measure the winding deviation amount Δz.

Further, when the length "a" of the long axis is made 180 μm or more and less than 200 μm (90% or more and less than 100% of the total thickness), the measurement light applied to the second sheet member 203b is slightly weaker than that when the length "a" of the long axis of the irradiation spot 209 is 200 μm. However, on the other hand, the amount of a reduction in the SS-OCT signal strength caused by the above length is small. Therefore, no problem occurs in the measurement of the position z1 and the position z2. However, the inventors of the present application have found out that, when the length "a" of the long length is made less than 180 μm (less than 110% of the total thickness), it is not possible to accurately measure the position z1 and the position z2.

As described above, the range of the length "a" of the long axis of the irradiation spot 209 is set to 90% or more and 110% or less of the total thickness of the first sheet member 202 and the second sheet member 203 which are stuck together.

As the beam diameter forming mechanism 310 of FIG. 2 which forms the shape of the irradiation spot 209, a cylindrical lens, a toroidal lens, an aperture, or the like can be used. Further, in FIG. 1A, the position of the side face part of the first sheet member 202 differs from the position of the side face part of the second sheet member 203 in the z-axis direction. Therefore, the beam diameter forming mechanism 310 of FIG. 2 is designed so that the shape of the irradiation spot hardly vary between the side face part of the first sheet member 202 and the side face part of the second sheet member 203.

A length "b" of a short axis of the irradiation spot 209 is as follows.

When the length "b" of the short axis of the irradiation spot 209 is made large, the resolution for the winding deviation amount Δz in the θ direction in FIG. 4A is reduced. Therefore, it is not possible to accurately measure a rapid change in the winding deviation amount Δz. When the resolution in the θ direction required for accurately measuring the winding deviation amount Δz is denoted by Δθ and the diameter of the wound body 204 is denoted by 2R, the length "b" of the short axis of the irradiation spot 209 required for preventing a reduction in the resolution in the θ direction is represented by the following Equation (2).

$$b < R \times \Delta\theta \qquad \text{Equation (2)}$$

For example, when Δθ=1° and R=9 mm, the length "b" of the short axis of the irradiation spot 209 is 157 μm or less from Equation (2).

When the total thickness of the first sheet member 202 and the second sheet member 203 is thin, the length "a" of the long axis of the irradiation spot 209 becomes small. When the required resolution Δθ in the θ direction is low, the length "b" of the short axis of the irradiation spot 209 becomes large. In such a case, the spot shape of the irradiation spot 209 is not necessarily formed in an elliptical shape. However, when the wound body 204 constitutes a lithium ion battery, the total thickness of the sheet members included therein is approximately 100 μm to 500 μm. Further, it is desirable that the θ-direction resolution Δθ be higher. Therefore, the irradiation spot 209 is preferably formed in an elliptical shape. In this case, for example, the length "b" of the short axis of the irradiation spot 209 is made approximately half or less of the length "a" of the long axis.

<Position of Irradiation Spot 209>

The irradiation spot 209 is desirably located between the contact point 210 and any point M (any position on the side face parts of the first sheet member 202 and the second sheet member 203 between the sticking roll 205 and the contact point 210), and more desirably located at the same position as the contact point 210 of the winding in FIG. 7A. The contact point 210 indicates any point at which the first sheet member 202 and the second sheet member 203 which have passed through the sticking roll 205 tangentially makes contact with the wound body 204 which is being formed on the winding core 206. In other words, the contact point 210 indicates a point at which the first sheet member 202 makes contact with a part of the second sheet member 203, the part being already wound to form the wound body 204.

After passing through the contact point 210, the first sheet member 202 and the second sheet member 203 are wound on the winding core 206. Therefore, the winding deviation amount Δz hardly varies.

If the measurement is performed at the point M, the following problem occurs. The first sheet member 202 and the second sheet member 203 do not receive the restriction force in the z-axis direction between the point M and the contact point 210. Therefore, the first sheet member 202 and the second sheet member 203 may displace in the z-axis direction because of factors such as variations of the sheet members in the material characteristics such as thickness between the first sheet member 202 and the second sheet member 203 and vibration of the winding core 206. That is, the winding deviation Δz may vary until the sheet members reach the contact point 210 and the accuracy in the measurement result may therefore be impaired. Thus, the measurement is more desirably performed at the contact point 210 of the winding. As an example, the dimension between the point M and the contact point 210 is 200 mm to 300 mm, and the diameter of the winding core 206 is approximately 10 mm to 50 mm. Further, the measurement point indicates the position of the irradiation spot 209.

However, because the first sheet member 202 and the second sheet member 203 are stuck together by the sticking roll 205, the possibility of the winding deviation amount Δz largely varying between the point M and the contact point 210 is not high. Therefore, the irradiation spot 209 may also be arranged not on the contact point 210, but on the point M. However, as described above, it is more preferred to arrange the irradiation spot 209 on the contact point 210. In this case, the position of the irradiation spot 209 is set so that the side face part of the first sheet member 202 and the side face part of the second sheet member 203 are located within the irradiation spot 209.

The position of the irradiation spot 209 of the measurement light is adjusted by the measurement head 307 of FIG. 2 which functions as an example of a first optical member. The measurement light is applied to a position that is located on the side face part 204e as well as between the contact point 210 and the sticking roll 205, by the measurement head 307 as the first optical member. Preferably, the measurement light is applied to a position that is located on the side face part 204e as well as on the contact point 210.

The position of the irradiation spot 209 is preferably moved depending on the rotation angle of the winding core 206 and the total thickness of the first sheet member 202 and the second sheet member 203. For example, when the thickness of the first sheet member 202 and the thickness of the second sheet member 203 are respectively denoted by "T1" and "T2" and the rotation speed of the winding core 206 is denoted by dθ/dt, the total thickness of the first sheet member 202 and the second sheet member 203 is (T1+T2), and the position of the irradiation spot 209 is desirably moved in the radial direction, or the y-axis direction of FIG. 1A by the following value (Equation (3)).

$$(T1+T2) \times (d\theta/dt)/360° \qquad \text{Equation (3)}$$

For example, when both the thickness "T1" and the thickness "T2" are 100 m and the rotation speed dθ/dt is 3600°/sec, the position of the irradiation spot 209 is moved in the y-axis direction at 2000 μm/sec from Equation (3).

The position of the irradiation spot 209 is moved by changing the angle of the galvano mirror 309 by the processor 314c of FIG. 2. Further, instead of using the galvano mirror 309, a mechanism such as a stepping motor may be provided, and the measurement head 307 itself may be moved by the processor 314c.

Generally, a separator is thin and has no rigidity. Therefore, the separator may lose the tension because of moisture absorption caused by the lapse of time, and may cover the electrode. Further, also when detaching the completed wound body 204 from the winding core 206, the separator may cover the electrode because of vibration or physical contact during the detachment. When the separator covers the electrode, it is difficult to obtain an SS-OCT signal from the electrode which is hidden behind the separator.

Figure 8A:
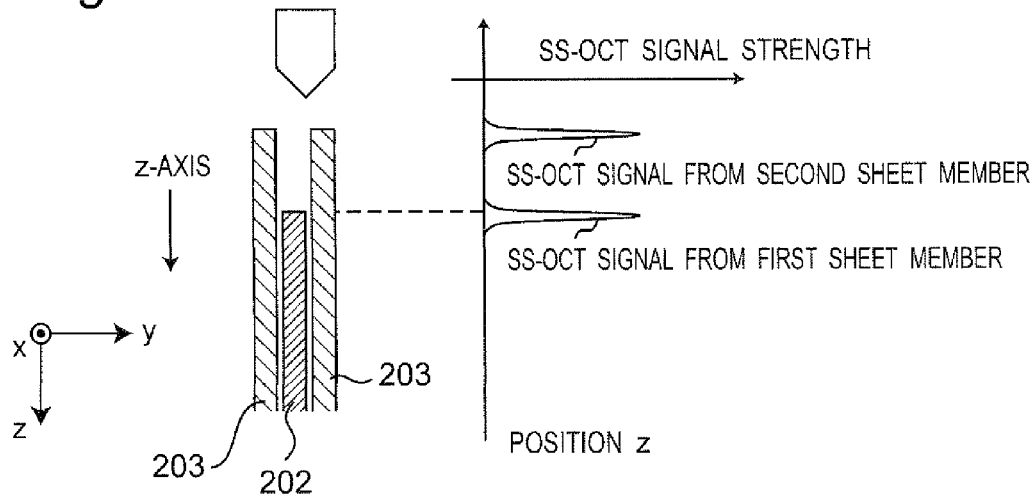
FIG. 8A is a view illustrating the relationship between a first sheet member and a second sheet member, specifically, an explanatory view illustrating the correspondence relationship between a view of the wound body with the first sheet member and the second sheet member maintaining the tension and a view illustrating the relationship between the SS-OCT signal and the position z.
Figure 8B:
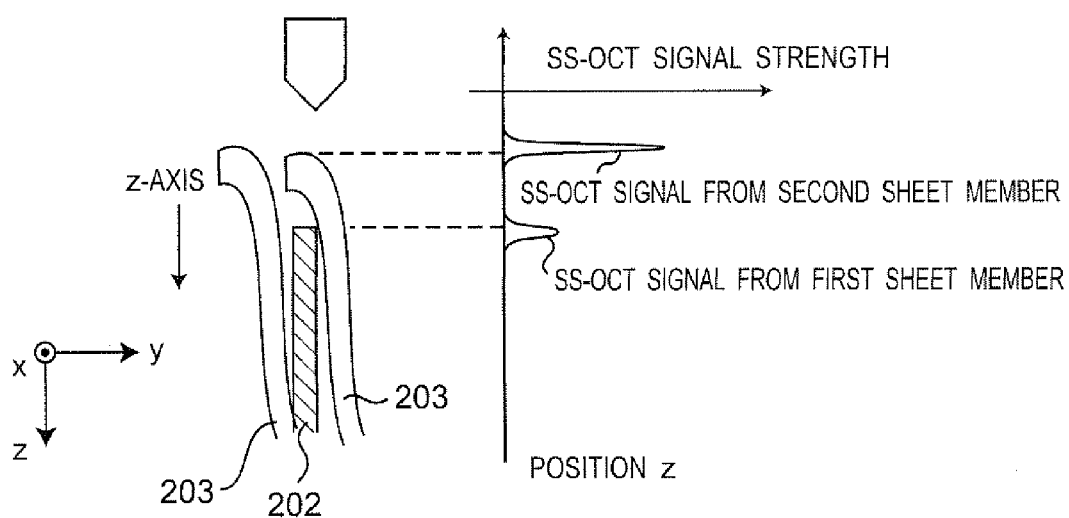
FIG. 8B is a view illustrating the relationship between the first sheet member and the second sheet member, specifically, an explanatory view illustrating the correspondence relationship between a view of the wound body with the second sheet member covering the second sheet member and a view illustrating the relationship between the SS-OCT signal and the position z.

FIG. 8A is an explanatory view illustrating the correspondence relationship between a view illustrating a state in which the second sheet member 203 as the separator immediately after being wound maintains the tension and a view illustrating the relationship between the SS-OCT signal strength and the position z. FIG. 8B is an explanatory view illustrating the correspondence relationship between a view illustrating a state in which the second sheet member 203 covers the first sheet member 202 as the electrode and a view illustrating the relationship between the SS-OCT signal strength and the position z. FIG. 8B clearly shows that the strength of the SS-OCT signal from the first sheet member 202 is weakened. This phenomenon of the separator covering the electrode may occur after the separator and the electrode pass through the contact point 210 of FIG. 7A. Therefore, it is desirable to arrange the irradiation spot 209 on the contact point 210 to perform the SS-OCT measurement.

Infrared light is used as the radiant light from the SS-OCT device 201. More specifically, near-infrared light having a wavelength of 0.8 μm or more and 1.4 μm or less is used as the radiant light from the SS-OCT device 201. Because near-infrared light penetrates a resin, the position of the electrode can be detected even when the separator made of a resin covers the electrode. However, the strength of the detected SS-OCT signal decreases when near-infrared light is absorbed or scattered at penetrating of the separator. Therefore, it is more desirable to measure the positions of the first sheet member 202 and the second sheet member 203 at the contact point 210 in the middle of performing the winding as described above.

Although the accuracy of the measurement is reduced compared to infrared light, light having a wavelength of 0.4 to 5 μm can be used as the radiant light in principle.

The first supply reel 50, the second supply reel 51, and the sticking roll 205 of FIG. 1A are each freely rotatable. However, the first supply reel 50, the second supply reel 51, and the sticking roll 205 may be each provided with a rotation drive device such as a motor. In this case, the rotation drive device is controlled by the winding controller 100.

In the first embodiment, the winding deviation of the wound body 204 is inspected while performing the winding by the winding apparatus. Therefore, a cycle time from the start of the winding until the completion of the inspection of the winding deviation can be reduced. Further, the winding apparatus according to the first embodiment can perform the inspection without using X-rays.

The measurement light may be applied to both sides of the first sheet member 202 and the second sheet member 203, that is, both side face parts of the wound body 204 to measure the positions from both sides. In this case, two SS-OCT devices 201 are used.

When the measurement light is applied to both end faces of the wound body 204, information about the first sheet member 202 and the second sheet member 203 in the width direction can be obtained. Specifically, the information about the first sheet member 202 and the second sheet member 203 in the width direction is obtained by obtaining the difference between the positions of both sides of the first sheet member 202 and the second sheet member 203. This is effective to know the configurations of the first sheet member 202 and the second sheet member 203. This method uses the fact that a separator is generally wider than an electrode.

Further, although the cycle time becomes longer, the inspection of the winding deviation may also be performed after the completion of the winding, that is, after the wound body 204 as an example of a component of the structural object is formed. In this case, the SS-OCT device 201 functions as an example of the inspection device which inspects the wound body 204 which includes the first sheet member 202 and the second sheet member 203 which are stuck together (an example of the component of the structural object). In addition to the wound body 204, a laminated type structural object such as a laminated battery can also be inspected. The inspection device is provided with a light source unit (the swept source type light source 302 as an example) which emits radiant light, a splitter (the first coupler 303 as an example) which splits the radiant light into measurement light which is applied to the side face part of the first sheet member 202 and the second sheet member 203 and reference light which is applied to a reference surface, an interference detector (the Fourier transformation circuit 314b as an example) which detects interference light formed by interference between the reference light reflected by the reference surface and the measurement light reflected by the side face part, a position detection processor (the processor 314c as an example) which detects a positions of the first sheet member 202 and the position of the second sheet member 203 on the basis of the detected interference light, and a decision processor (the decision processor 100c as an example) which decides the quality of the component on the basis of the detected positions of the first sheet member 202 and the second sheet member 203.

Further, the inspection method of the first embodiment may be performed using the SS-OCT device 201 which functions as an example of the inspection device. Further, the structural object manufacturing method including the inspection method may be achieved using the SS-OCT device 201 which functions as an example of the inspection device.

Second Embodiment

Figure 9:
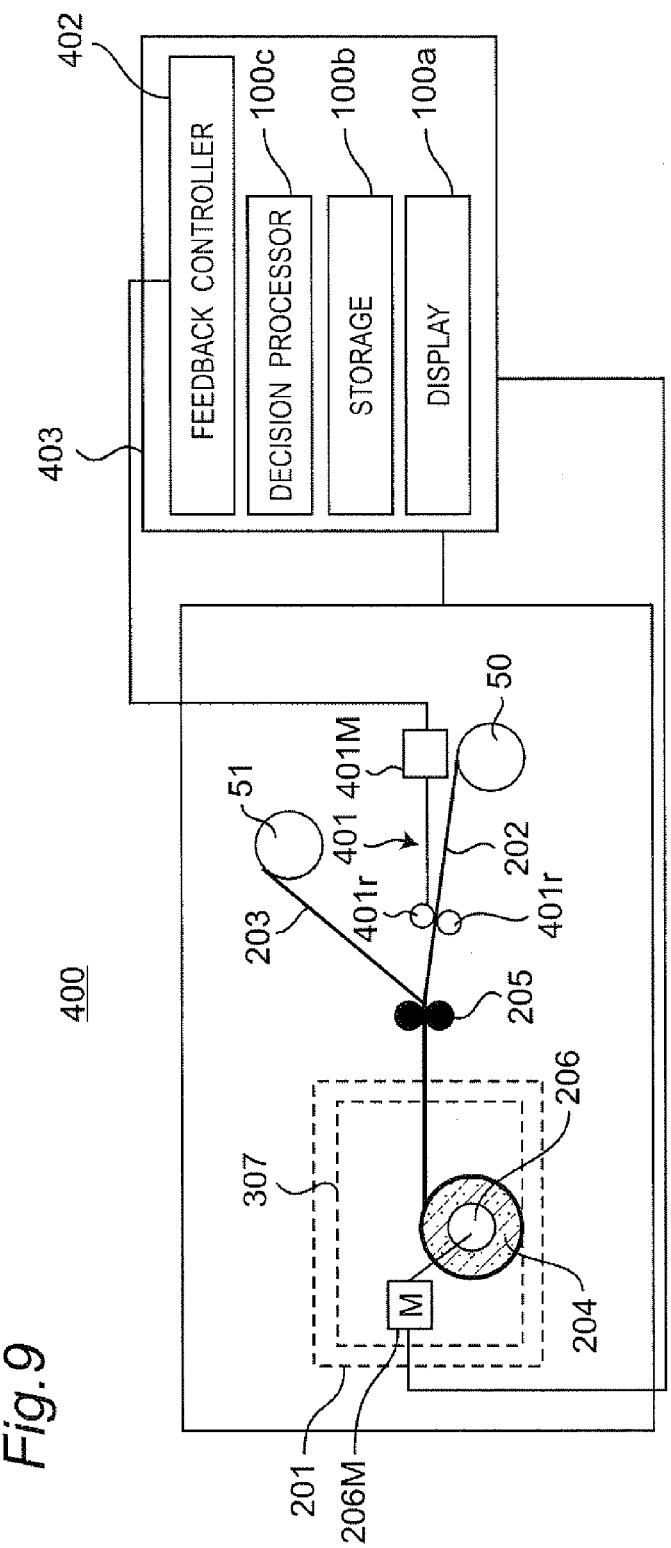
FIG. 9 is a schematic view of a winding apparatus in a second embodiment.

FIG. 9 is a schematic view of a winding apparatus 400 in a second embodiment. The common configurations between the first embodiment and the second embodiment will be denoted by the same reference sings, and description thereof will be omitted.

The second embodiment is characterized in that a roll guider 401 and a feedback controller 402 are further provided in addition to the configuration of the first embodiment. The feedback controller 402 is added to the winding controller 100 to constitute a winding control unit 403.

The roll guider 401 includes a pair of rollers 401r which sandwiches a first sheet member 202 therebetween and a movement device 401M which controls the pair of rollers 401r to move the first sheet member 202 in the z-axis direction. By driving the movement device 401M, it is possible to adjust the position in the z-axis direction of the first sheet member 202 to thereby control the winding deviation amount Δz. More specifically, the roll guider 401 changes an inclination angle in the axial direction of the pair of rollers 401r on the basis of a control amount (feedback amount Va) from the feedback controller 402 to thereby adjust the position in the z-axis direction of the first sheet member 202.

The feedback controller 402 feed backs (outputs a feedback signal) the control amount based on the winding deviation amount Δz obtained using a SS-OCT device 201 to the movement device 401M of the first roll guider 401. The relationship between the winding deviation amount Δz and the control amount is previously stored as a relational expression or a table in a storage of the feedback controller 402. The feedback controller 402 determines the control amount using the previously stored relational expression or table.

The roll guider 401 may be any element as long as it has a function of adjusting the position in the z-axis direction of the first sheet member 202.

Further, a second roll guider which adjusts the position in the z-axis direction of a second sheet member 203 may be further provided to thereby simultaneously adjust both the position of the first sheet member 202 and the position of the second sheet member 203.

Although the roll guider 401 is arranged so as to sandwich the first sheet member 202, the arrangement of the roll guider 401 is not limited thereto. The roll guider 401 may also be arranged so as to sandwich the second sheet member 203.

Also in the winding apparatus according to the second embodiment, it is possible to perform the inspection without using X-rays.

As a modification example, in the first and second embodiments, the wound body 204 may also be formed in such a manner that the first sheet member 202 and the second sheet member 203 are wound on the winding core 206 while being stuck together directly from the first supply reel 50 and the second supply reel 51 without providing the sticking roll 205. In this case, it is preferred to apply the measurement light to a position that is located on the side face part 204e as well as on the contact point 210 by the measurement head 307 of FIG. 2 which functions as an example of a second optical member. However, it is more preferred to provide the sticking roll 205 because the occurrence of the winding deviation can be prevented.

By properly combining arbitrary embodiments or modification examples of the aforementioned various embodiments and the modification examples, the effects owned by each of them can be made effectual.

INDUSTRIAL APPLICABILITY

The winding apparatus, the winding method, the inspection device, and the structural object manufacturing method according to the present invention can be applied to a process for manufacturing a lithium ion battery, a film capacitor, or the like.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

The invention claimed is:

1. A winding apparatus that winds a first sheet and a second sheet that are stuck together on a winding core to form a wound body, the winding apparatus comprising:
   a drive that rotates the winding core to wind the first and second sheets around the winding core to form the wound body;
   a light source unit that emits radiant light;
   a splitter that splits the radiant light into measurement light and reference light;
   a measurement head that directs the measurement light to an end face of the wound together first and second sheets on an optical path, and directs the measurement light reflected from the end face of the wound together first and second sheets on said optical path, wherein a traveling direction of the measurement light coincides with an axial direction of the wound body;
   optics that direct the reference light to a reference surface; and
   an Optical Coherence Tomography (OCT) processor that detects a position of the first sheet and a position of the second sheet by detecting interference light formed by interference between the reference light reflected by the reference surface and the measurement light reflected by the end face.

2. The winding apparatus according to claim 1, wherein the OCT processor detects the position of the first sheet and the position of the second sheet by performing frequency analysis on a signal based on the detected interference light.

3. The winding apparatus according to claim 2, further comprising a feedback controller that outputs a feedback signal for adjusting a position of the first sheet or a position of the second sheet based on the detected positions of the first sheet and the second sheet.

4. The winding apparatus according to claim 3, wherein the light source unit includes a light source that emits radiant light having a wavelength that varies at a constant period.

5. The winding apparatus according to claim 4, wherein the radiant light is infrared light.

6. The winding apparatus according to claim 5, wherein the first sheet is an electrode and the second sheet is a separator.

7. The winding apparatus according to claim 6, further comprising a sticking roll that sticks the first sheet and the second sheet together.

8. The winding apparatus according to claim 7, further comprising an optical member, wherein
   the optical member irradiates, with the measurement light, a position that is located on the end face as well as between a contact point at which the first sheet and the second sheet start being wound on the wound body and the sticking roll.

9. The winding apparatus according to claim 8, wherein the optical member forms the measurement light so that a spot diameter of the measurement light in the end face is 90% or more and 110% or less of a total thickness of the first sheet and the second sheet.

10. The winding apparatus according to claim 9, wherein the optical member forms a spot shape of the measurement light applied to the end face into an elliptical shape with a long axis of the elliptical shaped spot perpendicular to a movement direction of the stuck together first and second sheets.

11. The winding apparatus according to claim 9, wherein the optical member forms a spot shape of the measurement light applied to the end face into an elliptical shape with a long axis of the elliptical shaped spot perpendicular to a movement direction of the first sheet and the second sheet stuck together, and such that a length of the long axis of the elliptical shaped spot in the end face is 90% or more and 110% or less of a total thickness of the first sheet and the second sheet.

12. The winding apparatus according to claim 2, wherein the OCT processor detects the position of the first sheet and the position of the second sheet based on peak shapes included in intensity distribution of the interference light obtained as a result of the frequency analysis.

13. The winding apparatus according to claim 1, further comprising an optical member, wherein
   the optical member irradiates, with the measurement light, a position that is located on the end face as well as on a contact point at which the first sheet and the second sheet start being wound on the wound body, and the optical member forms the measurement light so that a spot diameter of the measurement light in the end face is 90% or more and 110% or less of a total thickness of the first sheet and the second sheet.

14. An inspection device that inspects a wound body formed by winding a first sheet and a second sheet together, the inspection device comprising:
   a light source unit that emits radiant light;
   a splitter that splits the radiant light into measurement light and reference light;
   a measurement head that directs the measurement light to an end face of the wound together first and second sheets on an optical path, and directs the measurement light reflected from the end face of the wound together first and second sheets on said optical path, wherein a traveling direction of the measurement light coincides with an axial direction of the wound body;
optics that direct the reference light to a reference surface; and
an Optical Coherence Tomography (OCT) processor that detects a position of the first sheet and a position of the second sheet by detecting interference light formed by interference between the reference light reflected by the reference surface and the measurement light reflected by the end face.

15. The inspection device according to claim 14, further comprising an optical member that forms the measurement light so that a spot diameter of the measurement light in the end face is 90% or more and 110% or less of a total thickness of the first sheet and the second sheet.

16. A battery manufacturing method comprising:
inspecting the wound body using the inspection device according to claim 15; and
manufacturing a battery including the inspected wound body.

17. A capacitor manufacturing method comprising:
inspecting the wound body using the inspection device according to claim 14; and
manufacturing a capacitor including the inspected wound body.

18. A winding method comprising:
winding a first sheet and a second sheet that are stuck together on a winding core to form a wound body;
directing, with a measurement head, measurement light to an end face of the wound together first and second sheets on an optical path, and directing the measurement light reflected from the end face of the wound together first and second sheets on said optical path, wherein a traveling direction of the measurement light coincides with an axial direction of the wound body;
directing with optics the reference light to a reference surface; and
detecting, with an Optical Coherence Tomography (OCT) processor, an end face position of the first sheet and an end face position of the second sheet by detecting interference light formed by interference between the reference light reflected by the reference surface and the measurement light reflected by the end face positions of the first and second sheets.

19. The winding method according to claim 18, further comprising forming the measurement light so that a spot diameter of the measurement light in the end face is 90% or more and 110% or less of a total thickness of the first sheet and the second sheet.

20. The winding method according to claim 18, further comprising: forming a spot shape of the measurement light applied to the end face into an elliptical shape with a long axis of the elliptical shaped spot perpendicular to a movement direction of the stuck together first and second sheets.

21. A battery manufacturing method comprising:
preparing the wound body formed by the winding method according to claim 18; and
manufacturing a battery including the wound body.

22. A capacitor manufacturing method comprising:
preparing the wound body formed by the winding method according to claim 18; and
manufacturing a capacitor including the wound body.

23. An inspection device that inspects a component having a first sheet and a second sheet that are stuck together, the first sheet and the second sheet having different reflectances from each other, the inspection device comprising:
a light source unit that emits radiant light;
a splitter that splits the radiant light into measurement light and reference light;
a measurement head that directs the measurement light to an end face of the stuck together first and second sheets on an optical path, and directs the measurement light reflected from the end face of the stuck together first and second sheets on said optical path;
optics that direct the reference light to a reference surface; and
an Optical Coherence Tomography (OCT) processor that detects a position of the first sheet and a position of the second sheet by detecting interference light formed by interference between the reference light reflected by the reference surface and the measurement light reflected by the end face,
wherein the OCT processor distinguishes between the first sheet and the second sheet based on difference in the reflectances of the first sheet and the second sheet.

24. A battery manufacturing method comprising:
inspecting the component using the inspection device according to claim 23; and
manufacturing a battery using the inspected component.

25. A capacitor manufacturing method comprising:
inspecting the component using the inspection device according to claim 23; and
manufacturing a capacitor using the inspected component.

* * * * *